(12) United States Patent
Freudenreich et al.

(10) Patent No.: US 6,211,410 B1
(45) Date of Patent: Apr. 3, 2001

(54) METHOD FOR PRODUCING ORGANIC HYDROXYLAMINES

(75) Inventors: Johannes Freudenreich, München; Jürgen Stohrer, Pullach, both of (DE)

(73) Assignee: Consortium für elektrochemische Industrie GmbH, Munich (DE)

(*) Notice: Subject to any disclaimer, the term of this patent is extended or adjusted under 35 U.S.C. 154(b) by 0 days.

(21) Appl. No.: 09/555,003

(22) PCT Filed: Nov. 19, 1998

(86) PCT No.: PCT/EP98/07445

§ 371 Date: May 22, 2000

§ 102(e) Date: May 22, 2000

(87) PCT Pub. No.: WO99/28289

PCT Pub. Date: Jun. 10, 1999

(30) Foreign Application Priority Data

Dec. 2, 1997 (DE) .............................. 197 53 462

(51) Int. Cl.⁷ .................................. C07C 239/08
(52) U.S. Cl. ............................ 564/300; 564/301
(58) Field of Search ..................... 564/300, 301

(56) References Cited

U.S. PATENT DOCUMENTS

| | | |
|---|---|---|
| 3,441,610 | 4/1969 | Dietz et al. . |
| 3,694,509 | 9/1972 | Rylander et al. . |
| 3,927,101 | 12/1975 | Le Ludec . |
| 3,992,395 | 11/1976 | Ludec . |
| 5,166,435 | * 11/1992 | Sharma et al. ................. 564/300 |
| 5,831,093 | 11/1998 | Götz et al. . |

FOREIGN PATENT DOCUMENTS

| | | |
|---|---|---|
| 1001658 | 12/1976 | (CA) . |
| 23 27 412 | 12/1973 | (DE) . |
| 23 57 370 | 5/1974 | (DE) . |
| 2455238 | 5/1974 | (DE) . |
| 24 55 887 | 5/1975 | (DE) . |
| 2118369 | 10/1980 | (DE) . |
| 195 02 700 | 8/1996 | (DE) . |
| 0086363 | 4/1985 | (EP) . |
| 0147879 | 7/1985 | (EP) . |
| 0212375 | 3/1987 | (EP) . |
| 0321219 | 2/1994 | (EP) . |
| 1388523 | 3/1975 | (GB) . |
| 1428226 | 3/1976 | (GB) . |
| 54-24837 | 2/1979 | (JP) . |
| 9600610 | 1/1996 | (ZA) . |

OTHER PUBLICATIONS

R. G. Coombes in Comprehensive Organic Chemistry, Pegamon Press, Oxford–New York Toronto–Sydney–Paris–Frankfurt, vol. 2, Part 7 Sides 325–334, 1979.

English Derwent Abstract Conesp. to JP 54 24837, 1979.

* cited by examiner

*Primary Examiner*—Samuel Barts
(74) *Attorney, Agent, or Firm*—Collard & Roe, P.C.

(57) ABSTRACT

According to the inventive method for producing organic hydroxylamines, at least one organic nitro compound is partially hydrogenated in the presence of an organic base or ammonia, a trivalent phosphor compound and a hydrogenation catalyst. The invention is characterised in that quantities of the nitrogen base of more than 10 wt. % in relation to the organic nitro compound are used.

10 Claims, No Drawings

METHOD FOR PRODUCING ORGANIC HYDROXYLAMINES

Various processes have been described for preparing organic hydroxylamines, e.g. the electrochemical reduction of nitro compounds or the reduction of nitro compounds using metals such as zinc or amalgams. On an industrial scale, it is particularly the selective catalytic hydrogenation of organic nitro compounds which is utilized.

In the case of nitroaromatics, it is known that the catalytic hydrogenation proceeds via a number of stages. It is frequently not possible to isolate the nitrosoaromatics and arylhydroxylamines which occur as intermediates, since further reduction to the stable aniline derivative occurs.

In addition, selective preparation of arylhydroxylamines is made more difficult by secondary reactions. Thus, arylhydroxylamines disproportionate to form the corresponding nitrosoaromatics and aniline derivatives. These intermediates can undergo further reactions which lead to dimeric compounds such as azoxybenzenes, azobenzenes and hydrazobenzenes.

Suitable additives allow disproportionation and over-reduction to be suppressed in the hydrogenation of nitroaromatics, so that a selective preparation becomes possible.

DE-A-2118369 (corresponds to U.S. Pat. No. 3,694,509; inventors: P. N. Rylander et al.) describes a method for the selective preparation of arylhydroxylamines, in which nitroaromatics are hydrogenated by means of hydrogen in a neutral solvent in the presence of from 0.1 to 100 mol of dimethyl sulfoxide per mole of catalyst. The selectivity of the hydrogenation under these conditions is about 85%, so that the arylhydroxylamines obtained are still contaminated with large amounts of the corresponding aniline derivatives and the total yields of the arylhydroxylamines are low.

In EP-A-212375 (inventor: G. C. Davis), phosphines, phosphates, sulfides, sulfoxides and heterocyclic nitrogen compounds in the presence of up to 0.4 equivalents of a protic acid per mole of the nitro-aromatic compound are used as additives. In the case of the hydrogenation of ethyl p-nitrobenzoate, selectivities of up to 99% can be achieved. Further nitro compounds are not described. However, the addition of acids required in this method has an adverse effect on the preparation of acid-sensitive arylhydroxylamines.

EP-A-86363 (inventors: D. C. Caskey, D. W. Chapman) describes the use of divalent sulfur compounds in combination with ammonia, aliphatic amines, phosphine, aliphatic phosphines, arylphosphines and phosphite esters as reaction moderators for the selective hydrogenation of nitroaromatics to arylhydroxylamines. The achievable selectivities are in the range 89–92%. The inactivation or poisoning of the catalysts, in particular by means of sulfur-containing additives, leads to the catalysts usually losing a large part of their activity after only one cycle and having to be replaced or regenerated at considerable cost.

JP 54-24837 (inventor: T. Tsurutani) (C.A. 91,56604) discloses a process in which arylhydroxylamines are obtained by catalytic hydrogenation of unsubstituted or substituted nitrobenzenes in alcohols or ethers in which phosphorous acid, alkali metal salts of phosphorous acid, phosphorous esters, thiophosphorous esters, alkylphosphines or arylphosphines, alkyl or aryl aminophosphines, alkyl or aryl sulfides, carboalkoxyalkyl sulfides, alkyl or aryl mercaptans or thiophenes are present. In this process, the hydrogenation has to be stopped after consumption of two equivalents of hydrogen, based on the nitro compound, in order to avoid over-reduction to the corresponding anilines. The achievable selectivity is 67–98%.

A selective hydrogenation of nitrobenzenes using platinum or palladium catalysts in the presence of organic bases whose pK is less than 3.2 is described in DE-A-2327412 (corresponds to CA-A-1001658; inventor: J. le Ludec) and DE-A-2357370 (corresponds to GB-A-1428226; inventor: J. le Ludec). The organic base has to be used in excess relative to the nitro compound. In the case of the preferred bases piperidine and diethylamine, only modest yields of simply structured arylhydroxylamines can be achieved after work-up and purification: N-phenylhydroxylamine was able to be isolated in a yield of only 52% after hydrogenation of nitrobenzene in diethylamine as solvent (DE-A-2327412).

Further organic bases described for this type of catalytic hydrogenation of nitroaromatics are N-alkylated piperidines which may also be alkylated on the carbon atoms of the ring, pyrrolidines alkylated on the nitrogen atom and/or the carbon atoms of the ring, N-alkylated or N-cycloalkylated anilines which may also be alkylated on the carbon atoms of the ring and pyridine, alkylated pyridines, quinoline and isoquinoline (DE-A-2455238, corresponds to U.S. Pat. No. 3,927,101; inventor: J. le Ludec) and also, for the selective hydrogenation of chloronitro-aromatics, secondary and tertiary monoamines which bear alkyl or cycloalkyl groups (DE-A-2455887, corresponds to U.S. Pat. No. 3,992,395; inventor: J. le Ludec). Using pyridine as solvent, N-phenylhydroxylamine was able to be isolated in a yield of 83% (DE-A-2455238).

DE-A-19502700 (corresponds to ZA-A-9600610; inventors: N. Götz et al.) describes a method of selectively hydrogenating nitroaromatics using platinum catalysts or sulfur- or selenium-doped palladium catalysts, in which nitroaromatics are hydrogenated in the presence of an excess of N-substituted morpholines as reaction moderators. The selectivities described are up to 98%. A disadvantage of this process is the high price of the bases which are used in excess. Owing to the high boiling point of N-alkylated morpholines, removal of these bases requires a relatively high temperature.

Nitroaromatics and nitroaliphatics are reduced in inert solvents to the corresponding arylhydroxylamines or alkylhydroxylamines in the presence of less than 10% by weight of organic base (based on the mass of the nitro derivative) and with addition of trivalent or pentavalent organic phosphorus compounds (EP-A-0147879; inventors: A. H. Sharma, P. Hope). Good yields of arylhydroxylamines are obtained, in particular, when using the costly DMAP (N,N-dimethylaminopyridine) instead of pyridine (yield of N-phenylhydroxylamine is 88% when using DMAP, 76% when using pyridine). Here too, a disadvantage is again that high selectivities are achieved only when using costly bases which have high boiling points and are therefore difficult to separate off. When using organic bases in amounts of less than 10% by weight based on the nitroaromatics, large amounts of trivalent phosphorus compounds (0.1–5% by weight) are required for a selective reaction. This results in rapid deactivation of the catalyst.

U.S. Pat. No. 3,441,610 (inventors: J. W. Dietz, J. R. McWorther) describes the catalytic hydrogenation of nitroalkanes to give N-alkylhydroxylamines. Here, the hydrogenation is carried out using a palladium catalyst with addition of iron, cobalt or nickel cations in a liquid two-phase system comprising aqueous sulfuric acid and an immiscible organic solvent. Under such strongly acidic conditions, the loss of catalyst is considerable. In addition, such mixtures have a strongly corrosive action on the apparatuses used.

EP-A-0321219 (inventors: M. B. Sherwin, P. Pichaichanarong) describes a process for preparing aqueous solutions of alkylhydroxylamines which are stable on storage under anaerobic conditions by reduction of nitroaliphatics having 1–18 carbon atoms with addition of complexing agents such as EDTA. The storage stability of such solutions is achieved by reducing the concentration of transition metal ions present to less than 20 ppm.

It is an object of the invention to provide a process for preparing organic hydroxylamines which avoids the disadvantages mentioned in the discussion of the prior art, can be carried out simply and inexpensively in industry, gives high selectivities and yields and makes it possible to isolate the organic hydroxylamines under gentle conditions.

This object is achieved by a process in which at least one organic nitro compound is partially hydrogenated in the presence of an organic base or ammonia and a trivalent phosphorus compound and a hydrogenation catalyst, wherein the organic base or the ammonia is used in an amount of greater than 10% by weight based on the organic nitro compound.

The combination of organic base or ammonia in an amount of over 10% by weight based on the nitro compound with trivalent phosphorus compounds results in a significant increase in the selectivity compared to sole use of excess organic bases (DE-A-2327412, DE-A-2357370, DE-A-2455238, DE-A-2455887, DE-A-19502700).

In the following, organic bases and ammonia are referred to by the collective term "nitrogen base".

In the process of the invention, the selectivity of the reaction is independent of the type of nitrogen base used. The process thus makes it possible to use inexpensive and readily available nitrogen bases.

When using inexpensive open-chain primary, secondary and tertiary amines, good selectivities in the temperature range above 20° C. are achieved only with addition of trivalent phosphorus compounds, which has great advantages in process engineering terms because of the exothermic nature of the hydrogenation.

The choice of low-boiling nitrogen bases such as primary amines or ammonia makes it possible for the base to be separated easily from even very thermolabile organic hydroxylamines.

Since further reduction of the organic hydroxylamines formed to the corresponding amine derivatives is greatly slowed when using the process of the invention, no further uptake of hydrogen after uptake of two mole equivalents of hydrogen, based on the nitro compound, takes place even over a number of hours. The process of the invention therefore also makes it easier to determine the end point of the hydrogenation and simplifies implementation in industrial plants.

The solutions of alkylhydroxylamines obtained by the process of the invention are stable on storage under inert gas.

The present invention preferably provides a process for preparing organic hydroxylamines of the formula I or II

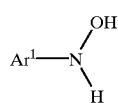

I

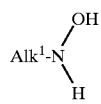

II where $Ar^1$ is an unsubstituted or substituted isocyclic or heterocyclic aryl radical and $Alk^1$ is an unsubstituted or substituted alkyl radical, by partial hydrogenation of organic nitro compounds of the formula III or IV $Ar^1\text{—}NO_2$     III $Alk^1\text{—}NO_2$     IV where $Ar^1$ and $Alk^1$ are as defined above, in the presence of a hydrogenation catalyst comprising at least one element of transition group VII or VIII of the Periodic Table and at least one nitrogen base and at least one trivalent phosphorus compound, wherein the nitrogen base and the nitro compound are used in a weight ratio of nitrogen base to nitro compound of greater than 0.1 and the trivalent phosphorus compound is used in an amount of 0.0001–3 mol % based on the nitro compound.

In the formulae I and III, $Ar^1$ is preferably an isocyclic or heterocyclic aryl radical which has one or two rings and may be substituted by one or more substituents $R^1$, where $R^1$ may be identical or different and each have one of the following meanings:

halogen atom, $C_1$–$C_4$-alkyl, halogen-($C_1$–$C_4$)-alkyl, halogen-($C_1$–$C_4$)-alkoxy, $C_1$–$C_4$-alkoxy, $C_1$–$C_4$-alkylthio, ($C_1$–$C_4$)-alkyl-carbonyl, ($C_1$–$C_4$)-alkoxycarbonyl, ($C_1$–$C_4$)-alkylaminocarbonyl, ($C_1$–$C_4$)-dialkylaminocarbonyl, ($C_1$–$C_4$)-dialkylamino, ($C_1$–$C_4$)-alkylamino, ($C_1$–$C_4$)-alkylcarbonylamino, ($C_1$–$C_4$)-alkylcarbonyl-($C_1$–$C_4$)-alkylamino, cyano, nitro, amino, hydroxy, carboxy, ester or salt of the carboxyl group, sulfono, ester or salt of the sulfono group or A–B, where A is —O—, —S—, —O—$CH_2$—, —$CH_2$—O—, —S—$CH_2$—, —$CH_2$—S—, —$CH_2$—O—CO—, —$CH_2$—N($R^2$)—, —CH=CH—, —CH=N—O— or a single bond, and $R^2$ is $C_1$–$C_4$-alkyl, $C_2$–$C_4$-alkenyl or hydrogen and B is phenyl, naphthyl, pyridinyl, pyrazinyl, pyrimidinyl, pyridazinyl, pyrazolyl, imidazolyl, oxazolyl, isoxazolyl, thiazolyl, isothiazolyl, furanyl, thienyl, pyrrolyl or $C_3$–$C_7$-cycloalkyl, where B may be substituted by 1–3 substituents $R^3$ and $R^3$ is halogen, $C_1$–$C_4$-alkyl, halo-($C_1$–$C_4$)-alkyl, halo-($C_1$–$C_4$)-alkoxy, $C_1$–$C_4$-alkoxy, $C_1$–$C_4$-alkylthio, ($C_1$–$C_4$)-alkylcarbonyl, ($C_1$–$C_4$)-alkoxycarbonyl, ($C_1$–$C_4$)-alkylaminocarbonyl, ($C_1$–$C_4$)-dialkylaminocarbonyl, ($C_1$–$C_4$)-alkylcarbonylamino, ($C_1$–$C_4$)-alkylcarbonyl-($C_1$–$C_4$)-alkylamino or cyano.

In the formulae II and IV, $Alk^1$ is preferably a linear or branched or cyclic alkyl radical having 1–24 carbon atoms, where the alkyl radical may be saturated or unsaturated and be unsubstituted or substituted by one or more substituents $R^4$, where $R^4$ may be identical or different and each have one of the following meanings:

$C_1$–$C_4$-alkoxy, $C_1$–$C_4$-alkylthio, ($C_1$–$C_4$)-alkylcarbonyl, ($C_1$–$C_4$)-alkoxycarbonyl, ($C_1$–$C_4$)-alkylaminocarbonyl, ($C_1$–$C_4$)-dialkylaminocarbonyl, ($C_1$–$C_4$)-dialkylamino, ($C_1$–$C_4$)-alkylamino, ($C_1$–$C_4$)-alkylcarbonylamino, ($C_1$–$C_4$)-alkylcarbonyl-($C_1$–$C_4$)-alkylamino, amino, hydroxy.

The process is particularly suitable for preparing N-phenylhydroxylamine.

Organic nitro compounds which can be used in the process of the invention are, for example, both simple nitroaromatics such as nitrobenzene, 2-nitrotoluene, 4-nitrotoluene, 4-nitrocumene, 2-nitro-m-xylene, 3-nitro-o-xylene, 4-nitro-o-xylene, 4-nitro-m-xylene, 5-nitro-m-xylene, nitromesitylene, nitroanthracene, 1-nitronaphthalene, 2-nitronaphthalene, 1-nitropyrene, 2-methyl-1-nitronaphthalene and 2-nitrofluorene and also more complex compounds such as 2-nitroanisole, 3-nitroanisole, 4-nitroanisole, 4-nitrobiphenyl, 2-nitrobenzenesulfonamide, 5-nitroquinoline, 8-nitroquinoline, 2-nitroimidazole, 5-nitroindazole, 6-nitroindoline, 5-nitroisoquinoline, 4-nitro-α-naphthol methyl ether, 4-nitrophenol, 4-nitroaniline, nitroresorcinol, 2-nitropyridine, 4-nitrobenzamide, 4-nitrobenzonitrile and 4-nitro-2,1,3-benzothiazole as well as nitroaliphatics such as nitromethane, nitro-tert-butane, 1-nitrobutane, 3-nitro-2-butanol, nitrocyclohexane, 1-nitrocyclohexene, nitrocyclopentane, nitroethane, 2-nitroethanol, 1-nitrohexane, 1-nitropropane, 2-nitropropane, 2-nitro-1-propanol, 2-nitro-1-propylamine and 2-nitro-1-ethylamine.

Among the nitroaromatics, preference is given to nitrobenzene, 2-nitrotoluene, 4-nitrotoluene, 4-nitrocumene, 2-nitro-m-xylene, 3-nitro-o-xylene, 4-nitro-o-xylene, 4-nitro-m-xylene, 5-nitro-m-xylene, nitromesitylene, nitroanthracene, 1-nitronaphthalene and 2-nitronaphthalene.

Among the nitroaliphatics, preference is given to nitromethane, nitro-tert-butane, 1-nitrobutane, nitrocyclohexane, 1-nitropropane and 2-nitropropane.

The nitroaromatics and nitroaliphatics used as starting materials are commercially available or can be prepared by simple means in a known manner and in good yields (R. G. Coombes in Comprehensive Organic Chemistry, Pergamon Press, Oxford—New York—Toronto—Sydney—Paris—Frankfurt, Vol. 2, Part 7, 325–334, 1979).

The hydrogenation catalyst used in the process of the invention may, if desired, be doped with silver, gold, copper, tin, sulfur, selenium or combinations of these elements.

The hydrogenation catalyst is preferably used in supported form.

Suitable support materials are preferably selected from the group consisting of porous or nonporous types of carbon having a low or high specific surface area, oxidic or salt-like compounds such as aluminum oxides, silicates, calcium carbonate, barium carbonate, barium sulfate, titanium dioxide and combinations of these materials.

Furthermore, the catalyst can also be applied to solvent-inert metals such as iron, copper, nickel, lead, tantalum, titanium, molybdenum, chromium, vanadium or alloys of these metals, if desired doped with carbon.

Preferred catalysts are platinum, palladium and nickel.

Particularly preferred catalysts are platinum and palladium.

Preferred support materials are porous or nonporous types of carbon, combinations of porous or nonporous types of carbon with oxidic or salt-like compounds and the solvent-inert metals iron, copper, titanium, tantalum, vanadium and their undoped or carbondoped alloys.

If the catalyst is fixed to a support material, then the catalyst content is preferably 0.1–20% by weight, particularly preferably 0.1–10% by weight and very particularly preferably 0.1–4% by weight, based on the support material.

The amount of catalyst metal used is preferably from 0.001 to 1% by weight, particularly preferably from 0.001 to 0.1% by weight, based on the nitro compound used.

The nitrogen base used in the process of the invention is preferably a compound selected from the group consisting of ammonia, monoalkylamines, dialkylamines, trialkylamines, monoalkanolamines, dialkanolamines, trialkanolamines, (poly)alkylenepolyamines, N-alkylated piperidines and morpholines which may also be alkylated on the carbon atoms of the ring, pyrrolidines alkylated on the nitrogen atom and/or the carbon atoms of the ring, N-alkylated anilines which may also be alkylated on the carbon atoms of the ring and pyridine, alkylated pyridines, quinoline and isoquinoline.

The abovementioned alkyl and alkanol groups may be branched or unbranched and preferably have 1–20 carbon atoms, particularly preferably 1–6 carbon atoms and very particularly preferably 1–4 carbon atoms.

Examples of monoalkylamines, dialkylamines and trialkylamines are methylamine, ethylamine, 1-propylamine, 2-propylamine, pentylamine, hexylamine, heptylamine, octylamine, nonylamine, dimethylamine, diethylamine, dipropylamine, diisopropylamine, dipentylamine, dihexylamine, diheptylamine, dioctylamine, trimethylamine, triethylamine, tripropylamine, ethyldimethylamine, diethylmethylamine, triisopropylamine, tributylamine, tripentylamine, trihexylamine, triheptylamine, trioctylamine and cyclohexylamine.

Examples of monoalkanolamines, dialkanolamines and trialkanolamines are ethanolamine, propanolamine, butanolamine, diethanolamine and triethanolamine.

Examples of (poly)alkylenepolyamines are ethylenediamine, diethylenetriamine, triethylenetetramine and tetraethylenepentamine.

Examples of pyrrolidines, piperidines and morpholines are pyrrolidine, piperidine, morpholine and monomethyl-, dimethyl-, trimethyl- and tetramethyl-pyrrolidines, -piperidines and -morpholines, N-methylpiperidine, N-methylmorpholine, N-methylpyrrolidine, N-ethylpiperidine, N-ethylmorpholine and N-ethylpyrrolidine.

Examples of anilines and pyridines are aniline, o- and m-toluidine, 2-ethylaniline, 3-ethylaniline, 4-ethylaniline, pyridine, 2-picoline, 3-picoline, 4-picoline and 2-ethylpyridine.

Preference is given to using a compound selected from the group consisting of ammonia, monoalkylamines, dialkylamines and trialkylamines, morpholines and piperidines.

Particular preference is given to using a compound selected from the group consisting of ammonia and monoalkylamines, dialkylamines and trialkylamines such as methylamine, ethylamine, 1-propylamine, 2-propylamine, pentylamine, hexylamine, heptylamine, octylamine, nonylamine, dimethylamine, diethylamine, dipropylamine, diisopropylamine, dipentylamine, dihexylamine, diheptylamine, dioctylamine, trimethylamine, triethylamine, tripropylamine, ethyldimethylamine, diethylmethylamine, triisopropylamine, tributylamine, tripentylamine, trihexylamine, triheptylamine, trioctylamine and cyclohexylamine.

The nitrogen bases can be used individually or as mixtures, and the amount of base used has to be such that the weight ratio of nitrogen base used/nitro compound used is greater than 0.1. The weight ratio is preferably in the range from 0.1 to 10.

In the process of the invention, preference is given to using trivalent phosphorus compounds in which the phosphorus atom bears one or more aryl or aryloxy groups and/or alkyl or alkoxy groups whose chain length is 1–20 carbon atoms, where the aryl groups may be unsubstituted or substituted by $C_1$–$C_4$-alkyl or $C_1$–$C_4$-alkoxy groups.

Examples of such compounds are triphenyl phosphite, dimethyl phenyl phosphite, triphenylphosphine, diphenyl phosphite, di-p-nitrophenyl phosphite and di-p-methylphenyl phosphite, trimethylphosphine, triethylphosphine, tripropylphosphine, triisopropylphosphine, tributylphosphine, trioctylphosphine, trimethyl phosphite, triethyl phosphite, triisopropyl phosphite, tripropyl phosphite, tributyl phosphite, trihexyl phosphite, trilauryl phosphite, tridecyl phosphite and trinonyl phosphite.

Preference is given to phosphorus compounds in which the phosphorus atom bears one or more phenyl or phenoxy groups and/or one or more alkyl or alkoxy groups whose chain length is 1–8 carbon atoms.

Further trivalent phosphorus compounds which can be used in the process of the invention are phosphorus trichloride and phosphorous acid.

The trivalent phosphorus compounds can be used individually or as mixtures.

The trivalent phosphorus compound should preferably be present in the initial reaction mixture in amounts of 0.0001–3 mol % based on the nitro compound, preferably in amounts of 0.0001–0.8 mol % and most preferably in amounts of 0.0001–0.1 mol %.

The process of the invention is preferably carried out in the temperature range from −10° C. to 100° C., preferably from 10° C. to 80° C.

To ensure that the hydrogenation proceeds sufficiently quickly at the temperature selected, preference is given to setting a hydrogen partial pressure in the range from atmospheric pressure to 10 bar gauge pressure.

The reaction can be carried out in the presence of further solvents such as ethers, esters, alcohols, nitriles, amides, aliphatic or aromatic hydrocarbons or water.

The arylhydroxylamines obtained by the process of the invention can, as is known from the literature, be converted into preparatively useful substituted aminophenols via the Bamberger rearrangement.

Furthermore, arylhydroxylamines are, as is known, used as starting materials for diarylnitrones which are used in photolithography, as intermediates for the preparation of crop protection agents and as starting material for the preparation of cupferron, an analytical reagent.

The alkylhydroxylamines obtained by the process of the invention are widely used, in particular, as intermediates for the preparation of hydroxamic acids which are used in pharmacy and in crop protection.

The following examples illustrate the present invention.

EXAMPLE 1

68 mg of a catalyst comprising 5% by weight of platinum on activated carbon (from Aldrich) are placed in a 100 ml autoclave. 3.0 ml of nitrobenzene and 12.0 ml of diethylamine are then pipetted in. After addition of 3 $\mu$l of triethyl phosphite, the mixture is hydrogenated at 25° C. and a hydrogen pressure of 5 bar for 2 hours while stirring vigorously.

HPLC analysis of the crude mixtures indicates 96.6 mol % of phenylhydroxylamine, 1.4 mol % of aniline and 2 mol % of nitrobenzene.

COMPARATIVE EXAMPLE 1

The procedure of Example 1 is repeated, but without addition of triethyl phosphite.

HPLC analysis after a reaction time of 2 hours indicates 46.2 mol % of phenylhydroxylamine, 47.2 mol % of aniline and 6.6 mol % of nitrobenzene.

EXAMPLE 2

The procedure of Example 1 is repeated using triethylamine as solvent. The catalyst from a previous hydrogenation reaction is reused. 1.5 hours are required for complete reaction.

HPLC analysis indicates 97.3 mol % of phenylhydroxylamine, 1.0 mol % of aniline and 1.7 mol % of nitrobenzene.

COMPARATIVE EXAMPLE 2

The procedure of Example 2 is repeated, but without addition of triethyl phosphite. The hydrogenation is carried out for 2 hours at 20° C.

HPLC analysis indicates 62.9 mol % of phenylhydroxylamine, 16.2 mol % of nitrobenzene and 20.9 mol % of aniline.

EXAMPLE 3

The procedure of Example 1 is repeated using pyridine as solvent.

HPLC analysis after a reaction time of 3.75 hours indicates 97.3 mol % of phenylhydroxylamine, 2.4 mol % of aniline and 0.3 mol % of nitrobenzene.

COMPARATIVE EXAMPLE 3

The procedure of Example 3 is repeated, but without addition of triethyl phosphite. The reaction time is 4 hours.

HPLC analysis indicates 91.2 mol % of phenylhydroxylamine, 6.5 mol % of aniline and 2.3 mol % of nitrobenzene.

EXAMPLE 4

The procedure of Example 1 is repeated using N-methylmorpholine as solvent. The hydrogenation is carried out for 5 hours at 28° C.

HPLC analysis indicates 97.8 mol % of phenylhydroxylamine, 1.7 mol % of aniline and 0.5 mol % of nitrobenzene.

COMPARATIVE EXAMPLE 4

The procedure of Example 4 is repeated, but without addition of triethyl phosphite.

HPLC analysis after a reaction time of 5 hours indicates 85 mol % of phenylhydroxylamine, 14.6 mol % of aniline and 0.4 mol % of nitrobenzene.

EXAMPLE 5

45.9 mg of a catalyst comprising 1.2% by weight of platinum on activated carbon are placed in a 100 ml autoclave. 3.6 g of nitrobenzene and 12 ml of n-propylamine are then pipetted in. After addition of 1 $\mu$l of triethyl phosphite, the mixture is hydrogenated at 25° C. and 2 bar hydrogen pressure while stirring.

After a reaction time of 3.75 hours, HPLC analysis indicates 98.2 mol % of phenylhydroxylamine and 1.8 mol % of aniline.

COMPARATIVE EXAMPLE 5

The procedure of Example 5 is repeated without addition of triethyl phosphite.

HPLC analysis after a reaction time of 4.25 hours indicated 82.6 mol % of phenylhydroxylamine, 16.5 mol % of aniline and 0.9 mol % of nitrobenzene.

EXAMPLE 6

The procedure of Example 5 is repeated using i-propylamine as solvent. A catalyst comprising 5% by weight of platinum on activated carbon (from Aldrich) is added thereto. 2.5 hours are required for complete reaction.

HPLC analysis indicated 97.7 mol % of phenylhydroxylamine, 2.0 mol % of aniline and 0.3 mol % of nitrobenzene.

EXAMPLE 7

The procedure of Example 5 is repeated using a mixture of 6 ml of n-propylamine and 6 ml of toluene as solvent. 68 mg of a catalyst comprising 5% by weight of platinum on activated carbon (from Aldrich) are used. 3 hours are required for complete hydrogenation.

HPLC analysis indicated 93.2 mol % of phenylhydroxylamine, 3.9 mol % of aniline and 2.9 mol % of nitrobenzene.

EXAMPLE 8

The procedure of Example 5 is repeated using 68 mg of a catalyst comprising 5% by weight of platinum on activated carbon (from Aldrich). The triethyl phosphite is replaced by 4.6 mg of triphenyl phosphine. The mixture is treated with hydrogen gas for 3.75 hours for complete reaction.

HPLC analysis indicates 96.6 mol % of phenylhydroxylamine, 2.0 mol % of aniline and 1.4 mol % of nitrobenzene.

EXAMPLE 9

The procedure of Example 8 is repeated with the triphenylphosphine being replaced by 3.5 µl of tripropylphosphine.

HPLC analysis after a reaction time of 2.75 hours indicates 96.5 mol % of phenylhydroxylamine, 1.6 mol % of aniline and 1.9 mol % of nitrobenzene.

EXAMPLE 10

The procedure of Example 5 is repeated using 22.7 mg of a catalyst comprising 5% by weight of platinum on activated carbon (from Aldrich). The hydrogenation reaction is carried out at 60° C. A hydrogenation time of 2.5 hours gives, according to HPLC analysis, 95.3 mol % of phenylhydroxylamine, 2.0 mol % of aniline and 2.7 mol % of nitrobenzene.

EXAMPLE 11

31.5 mg of platinum powder (from Alfa, 99.9% with particle size 0.5–1.2 µm) are placed in a 100 ml autoclave. 3.6 g of nitrobenzene and 12 ml of n-propylamine are then pipetted in. After addition of 3 µl of triethylphosphite, the mixture is hydrogenated at 30° C. and 5 bar hydrogen pressure while stirring.

HPLC analysis after a reaction time of 2 hours indicated 95.4 mol % of phenylhydroxylamine, 2.0 mol % of aniline and 3.6 mol % of nitrobenzene.

EXAMPLE 12

110 mg of a catalyst comprising 1% of platinum on activated carbon are placed in a 100 ml autoclave. 5.09 g of 8-nitroquinoline and 20 ml of n-propylamine are added thereto. After addition of 3 µl of triethyl phosphite, the mixture is hydrogenated at 25° C. and a hydrogen pressure of 5 bar for 3 hours while stirring vigorously.

HPLC analysis indicates 100 mol % of 8-hydroxylaminoquinoline.

The crude mixture is freed of solvent at 40° C./20 mbar, dissolved in ethyl acetate and precipitated with petroleum ether. This gives a yellow powder having a melting point of 66–68° C.

1H-NMR (CD$_3$OD δ in ppm): 8.71 (dd, 1 H), 8.19 (dd, 1 H), 7.42 (m, 4 H).

EXAMPLE 13

92 mg of a catalyst comprising 1.2% of platinum on activated carbon are placed in a 100 ml autoclave. 15 ml of a mixture of 9.6 ml of nitrobenzene, 38.5 ml of n-hexanol and 1.9 ml of water are then pipetted in. 4.0 g of gaseous ammonia are passed into this mixture. After addition of 3 µl of triethyl phosphite, the mixture is hydrogenated at room temperature and 5 bar hydrogen partial pressure for 3.25 hours.

HPLC analysis indicates 95.25 mol % of phenylhydroxylamine, 3 mol % of aniline and 1.75 mol % of nitrobenzene.

EXAMPLE 14

110 mg of a catalyst comprising 1% of platinum on activated carbon are placed in a 100 ml autoclave. 15 ml of a mixture of 18.7 ml of nitrobenzene, 74.8 ml of n-butanol and 6.6 ml of water are then pipetted in. 7.9 g of gaseous ammonia are passed into this mixture. After addition of 3 µl of triethyl phosphite, the mixture is hydrogenated at room temperature and 5 bar hydrogen partial pressure for 2.25 hours.

HPLC analysis indicates 96 mol % of phenylhydroxylamine, 1.5 mol % of nitrobenzene and 2.5 mol % of aniline.

EXAMPLE 15

110 mg of a catalyst comprising 1% of platinum on activated carbon are placed in a 100 ml autoclave. 3 ml of nitrobenzene and 12 ml of a 7 N ammonia solution in methanol are then pipetted in. After addition of 3 µl of triethyl phosphite, the mixture is hydrogenated at room temperature and 5 bar hydrogen partial pressure for 5.25 hours.

HPLC analysis indicates 95 mol % of phenylhydroxylamine, 3.3 mol % of aniline and 0.7 mol % of nitrobenzene.

What is claimed is:

1. A process for preparing organic hydroxylamines, in which an organic nitro compound is partially hydrogenated in the presence of an organic base or ammonia, a trivalent phosphorus compound and a hydrogenation catalyst, wherein the organic base is used in an amount of greater than 10% by weight based on the organic nitro compound.

2. A process for preparing organic hydroxylamines of the formula I or II

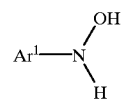

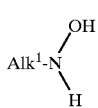

where $Ar^1$ is an unsubstituted or substituted isocyclic or heterocyclic aryl radical and $Alk^1$ is an unsubstituted or substituted alkyl radical, by partial hydrogenation of organic nitro compounds of the formula III or IV

where $Ar^1$ and $Alk^1$ are as defined above, in the presence of a hydrogenation catalyst comprising at least one element of transition group VII or VIII of the Periodic Table and at least one nitrogen base and at least one trivalent phosphorus compound, wherein the nitrogen base and the nitro compound are used in a weight ratio of nitrogen base to nitro compound of greater than 0.1 and the trivalent phosphorus compound is used in an amount of 0.0001–3 mol % based on the nitro compound.

3. A process as claimed in claim 2, wherein $Ar^1$ in the formulae I and III is an isocyclic or heterocyclic aryl radical which has one or two rings and may be substituted by one or more substituents $R^1$, where $R^1$ may be identical or different and each have one of the following meanings: halogen atom, $C_1$–$C_4$-alkyl, halogen-($C_1$–$C_4$)-alkyl, halogen-($C_1$–$C_4$)-alkoxy, $C_1$–$C_4$-alkoxy, $C_1$–$C_4$-alkylthio, ($C_1$–$C_4$)-alkylcarbonyl, ($C_1$–$C_4$)-alkoxycarbonyl, ($C_1$–$C_4$)-alkylaminocarbonyl, ($C_1$–$C_4$)-dialkylaminocarbonyl, ($C_1$–$C_4$)-dialkylamino, ($C_1$–$C_4$)-alkylamino, ($C_1$–$C_4$)-alkylcarbonylamino, ($C_1$–$C_4$)-alkylcarbonyl-($C_1$–$C_4$)-alkylamino, cyano, nitro, amino, hydroxy, carboxy, ester or salt of the carboxyl group, sulfono, ester or salt of the sulfono group or A–B,
where A is —O—, —S—, —O—CH$_2$—, —CH$_2$—O—, —S—CH$_2$—, —CH$_2$—S—, —CH$_2$—O—CO—, —CH$_2$—N(R$^2$)—, —CH=CH—, —CH=N—O— or a single bond, and
$R^2$ is $C_1$–$C_4$-alkyl, $C_2$–$C_4$-alkenyl or hydrogen and
B is phenyl, naphthyl, pyridinyl, pyrazinyl, pyrimidinyl, pyridazinyl, pyrazolyl, imidazolyl, oxazolyl, isoxazolyl, thiazolyl, isothiazolyl, furanyl, thienyl, pyrrolyl or $C_3$–$C_7$-cycloalkyl,
where B may be substituted by 1–3 substituents $R^3$ and $R^3$ is halogen, $C_1$–$C_4$-alkyl, halo-($C_1$–$C_4$)-alkyl, halo-($C_1$–$C_4$)-alkoxy, $C_1$–$C_4$-alkoxy, $C_1$–$C_4$-alkylthio, ($C_1$–$C_4$)-alkylcarbonyl, ($C_1$–$C_4$)-alkoxycarbonyl, ($C_1$–$C_4$)-alkylaminocarbonyl, ($C_1$–$C_4$)-dialkylaminocarbonyl, ($C_1$–$C_4$)-alkylcarbonylamino, ($C_1$–$C_4$)-alkylcarbonyl-($C_1$–$C_4$)-alkylamino or cyano, and $Alk^1$ in the formulae II and IV is a linear or branched or cyclic alkyl radical having 1–24 carbon atoms, where the alkyl radical may be saturated or unsaturated and is unsubstituted or substituted by one or more substituents $R^4$, where $R^4$ may be identical or different and each have one of the following meanings: $C_1$–$C_4$-alkoxy, $C_1$–$C_4$-alkylthio, ($C_1$–$C_4$)-alkylcarbonyl, ($C_1$–$C_4$)-alkoxycarbonyl, ($C_1$–$C_4$)-alkylaminocarbonyl, ($C_1$–$C_4$)-dialkylaminocarbonyl, ($C_1$–$C_4$)-dialkylamino, ($C_1$–$C_4$)-alkylamino, ($C_1$–$C_4$)-alkylcarbonylamino, ($C_1$–$C_4$)-alkylcarbonyl-($C_1$–$C_4$)-alkylamino, amino, hydroxy.

4. A process as claimed in claim 1, wherein the organic nitro compounds used are simple nitroaromatics such as nitrobenzene, 2-nitrotoluene, 4-nitrotoluene, 4-nitrocumene, 2-nitro-m-xylene, 3-nitro-o-xylene, 4-nitro-o-xylene, 4-nitro-m-xylene, 5-nitro-m-xylene, nitromesitylene, nitroanthracene, 1-nitronaphthalene, 2-nitronaphthalene, 1-nitropyrene, 2-methyl-1-nitronaphthalene and 2-nitrofluorene and also more complex compounds such as 2-nitroanisole, 3-nitroanisole, 4-nitroanisole, 4-nitrobiphenyl, 2-nitrobenzenesulfonamide, 5-nitroquinoline, 8-nitroquinoline, 2-nitroimidazole, 5-nitroindazole, 6-nitroindoline, 5-nitroisoquinoline, 4-nitro-α-naphthol methyl ether, 4-nitrophenol, 4-nitroaniline, nitroresorcinol, 2-nitropyridine, 4-nitrobenzamide, 4-nitrobenzonitrile and 4-nitro-2,1,3-benzothiazole, or nitroaliphatics such as nitromethane, nitro-tert-butane, 1-nitrobutane, 3-nitro-2-butanol, nitrocyclohexane, 1-nitrocyclohexene, nitrocyclopentane, nitroethane, 2-nitroethanol, 1-nitrohexane, 1-nitropropane, 2-nitropropane, 2-nitro-1-propanol, 2-nitro-1-propylamine and 2-nitro-1-ethylamine.

5. A process as claimed in claim 1, wherein the nitrogen base used is ammonia, a monoalkylamine, dialkylamine, trialkylamine, monoalkanolamine, dialkanolamine, trialkanolamine or (poly) alkylenepolyamine, an N-alkylated piperidine or morpholine which may also be alkylated on the carbon atoms of the ring, a pyrrolidine alkylated on the nitrogen atom and/or the carbon atoms of the ring, an N-alkylated aniline which may also be alkylated on the carbon atoms of the ring, or pyridine an alkylated pyridine, quinoline or isoquinoline.

6. A process as claimed in claim 1, wherein the trivalent phosphorus compound used is at least one compound in which the phosphorus atom bears one or more aryl or aryloxy groups or alkyl or alkoxy groups whose chain length is 1–20 carbon atoms, where the aryl groups may be unsubstituted or substituted.

7. A process as claimed in claim 1, wherein the weight ratio of organic base used to nitro compound used is in the range from 1 to 5.

8. A process as claimed in claim 1, wherein the trivalent phosphorus compound is present in the initial reaction mixture in an amount of 0.0001–3 mol % based on the nitro compound.

9. A process as claimed in claim 1, wherein the catalyst is used in an amount of from 0.001 to 1% by weight based on the nitro compound used.

10. A process as claimed in claim 1, carried out in the temperature range from –10° C. to 100° C.

* * * * *